US00PP08399P

United States Patent [19]

Guillen

[11] Patent Number: Plant 8,399

[45] Date of Patent: Sep. 28, 1993

[54] NEW GUINEA IMPATIENS NAMED BSR-221 ELECTRIC PINK

[75] Inventor: Mario Guillen, Cartago, Costa Rica

[73] Assignee: George J. Ball, Inc., West Chicago, Ill.

[21] Appl. No.: 917,271

[22] Filed: Jul. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-221 Electric Pink is provided. This new cultivar was the result of a controlled breeding program wherein the Diane cultivar (U.S. Plant Pat. No. 6,683) was pollinated by a plant designated N2298-1 (nonpatented in the United States). The new cultivar forms attractive very large red-purple blossoms displaying an iridescent appearance combined with a strong basal branching character and an upright mounded growth habit and can be readily distinguished from the Aglia cultivar (U.S. Plant Pat. No. 6,684).

1 Drawing Sheet

SUMMARY OF THE INVENTION

The present invention comprises a new and distinctive Impatiens plant, botanically known as New Guinea Impatiens, and hereafter referred to by the cultivar name BSR-221 Electric Pink.

The new cultivar is the product of a planned breeding program. More specifically, the breeding program which resulted in the production of the new cultivar was carried out in a controlled environment during 1989 at Linda Vista, Cartago, Costa Rica. The female parent (i.e., the seed parent) was the Diane cultivar (U.S. Plant Pat. No. 6,683) which exhibits salmon red blossoms with dark green foliage. The male parent (i.e., the pollen parent) was a plant designated N2298-1 (nonpatented in the United States) which exhibits large deep salmon blossoms with dark green foliage. The parentage of the new cultivar can be summarized as follows:

Diane × N2298-1.

The seeds resulting from the above pollination were sown and plantlets were obtained which were physically and biologically different from each other. Selective study resulted in the identification of a single plant of the new cultivar. This plant had dark pink blossoms and initially was designated BSR-221.

It was found that the cultivar of the present invention:

(a) exhibits attractive very large red-purple blossoms displaying an iridescent appearance which commonly measure approximately 7.0 cm. in diameter and approximately 6.5 cm. in length
(b) exhibits a strong basal branching character, and
(c) exhibits an upright branched growth habit.

Asexual reproduction of the new cultivar by terminal or stem cuttings taken during February, 1990 at Santa Maria, Calif., has demonstrated that the characteristics of the new cultivar as herein described are firmly fixed and are retained through successive generations of such asexual propagation.

The BSR-221 Electric Pink cultivar has not been observed under all possible environmental conditions to date. Accordingly, it is possible that the phenotype may vary somewhat with variations in the environment, such as temperature, light intensity, and day length.

When the new cultivar of the present invention is compared to the Aglia cultivar (U.S. Plant Pat. No. 6,684), it is found that the new variety exhibits a growth habit which is not as compact or mounded as that of the Aglia cultivar. The flowers of the new cultivar are larger and exhibit an iridescence (as illustrated) which is lacking in the Aglia cultivar. The flowers of the Aglia cultivar commonly measure approximately 6.25 cm. in diameter and approximately 6.0 cm. in length. Also, the flowers of the new cultivar are more rounded than those of the Aglia cultivar which commonly display gaps between petals.

When plant material of the BSR-221 Electric Pink cultivar is subjected to standard random amplified polymorphic DNA marker analysis (RAPD) using polymerase chain reaction (PCR) and a known unique set of DNA primers, it is found to exhibit a different fingerprint map when compared to that of the Aglia cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Arroyo Grande, Calif., U.S.A.

DETAILED DESCRIPTION

The chart used in the identification of colors described herein is The R.H.S. Colour Chart of The Royal Horticultural Society, London, England. The color values were determined at Arroyo Grande, Calif., U.S.A., during the first week of January, 1992. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Strong basal branching.

*Habit of growth.*—Upright mounded. A mature plant commonly measures approximately 12 inches in height and approximately 15 inches in width.

*Foliage.*—The configuration is narrow and lanceolate. The leaves of the BSR-221 Electric Pink cultivar measure approximately 11.25 cm×3.75 cm. while those of the Aglia cultivar measure approximately 12.25 cm.×3.5 cm. The foliage of the BSR-221 Electric Pink cultivar is solid dark green, Green Group 137A, in the absence of variegation (abaxial) and Yellow-Green Group 148A with veins of Red Group 46A (adaxial). This can be compared to Green Group 141B at the margins and Yellow-Green Group 150B as central variegation (abaxial) and Green Group 130A with veins of Red Group 53A (adaxial) for the Aglia cultivar. The stem color is Red Group 46A while that of the Aglia cultivar is Red Group 53A.

Flower description:

*Flowering habit.*—Freely flowering.

*Natural flowering season.*—Year-round in greenhouse environment.

*Flowers borne.*—Above foliage, arising from leaf axils.

*Flower color.*—Red-Purple Group 58B (abaxial) and Red-Purple Group 58C (adaxial). This can be compared to Red-Purple Group 57B (abaxial) and Red-Purple Group 57D (adaxial) for the Aglia cultivar.

*Quantity of flowers.*—Approximately 5 to 10 per stem.

*Number of petals.*—Five.

*Flower diameter.*—Approximately 7.0 cm. which can be compared to approximately 6.25 cm. for the Aglia cultivar.

*Nectary length.*—Approximately 5.0 cm. which can be compared to approximately 5.25 cm. for the Aglia cultivar.

*Nectary color.*—Red Group 53A which can be compared to Red Group 53B for the Aglia cultivar.

*Reproductive organs.*—The anthers are fused together forming one organ that surrounds the pistil. Generally, the anthers shed pollen prior to the stigma becoming receptive. The pollen color is cream-white, White Group 155D. The stigma color is Red-Purple Group 67A and can be compared to Yellow-Green Group 144C exhibited by the Aglia cultivar. The ovary color is Red-Purple Group 59B and can be compared to Yellow-Green Group 144A exhibited by the Aglia cultivar.

I claim:

1. A new and distinct cultivar of New Guinea Impatiens named BSR-203 Electric Pink, substantially as herein shown and described, which:

(a) exhibits attractive very large red-purple blossoms displaying an iridescent appearance which commonly measure approximately 7.0 cm. in diameter and approximately 6.5 cm. in length, (b) exhibits a strong basal branching character, and (c) exhibits upright branched growth habit.

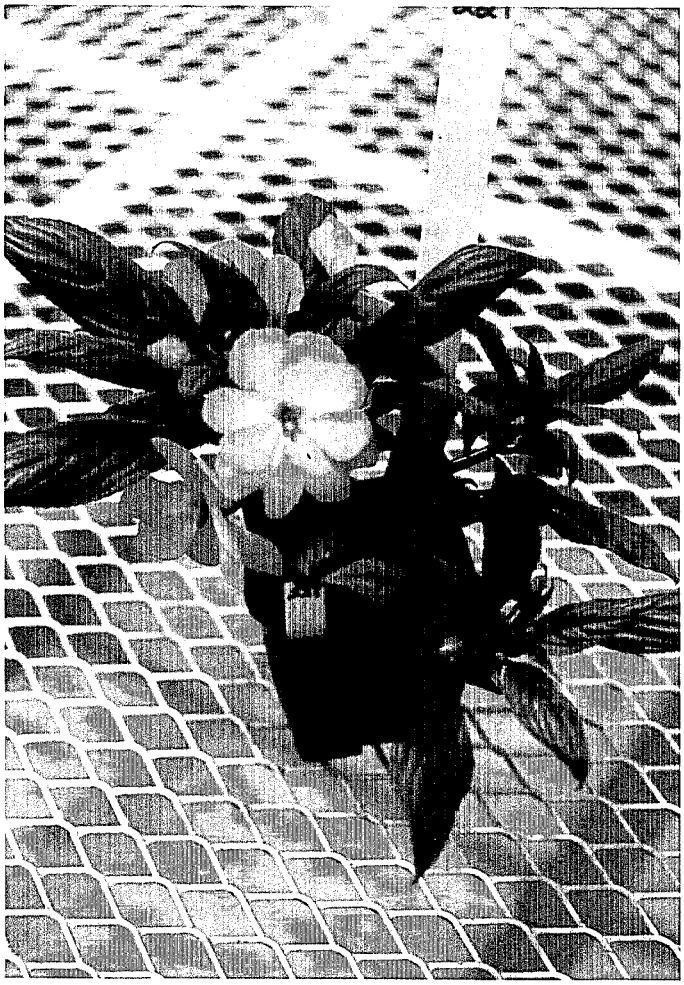

* * * * *